US010078121B2

(12) United States Patent
Bindseil et al.

(10) Patent No.: US 10,078,121 B2
(45) Date of Patent: *Sep. 18, 2018

(54) ACTIVE COIL TO SHIFT A VOLUME OF UNIFORM MAGNETIC FIELD

(71) Applicant: Synaptive Medical (Barbados) Inc., Bridgetown (BB)

(72) Inventors: Geron André Bindseil, Toronto (CA); Chad Tyler Harris, Toronto (CA)

(73) Assignee: Synaptive Medical (Barbados) Inc., Bridgetown (BB)

(*) Notice: Subject to any disclaimer, the term of this patent is extended or adjusted under 35 U.S.C. 154(b) by 0 days.

This patent is subject to a terminal disclaimer.

(21) Appl. No.: 15/788,141

(22) Filed: Oct. 19, 2017

(65) Prior Publication Data

US 2018/0038927 A1  Feb. 8, 2018

Related U.S. Application Data

(63) Continuation of application No. 14/899,799, filed as application No. PCT/IB2015/055366 on Jul. 15, 2015, now Pat. No. 9,797,967.

(51) Int. Cl.
*G01V 3/00* (2006.01)
*G01R 33/3875* (2006.01)
*G01R 33/381* (2006.01)
*A61B 5/055* (2006.01)

(52) U.S. Cl.
CPC ......... *G01R 33/3875* (2013.01); *A61B 5/055* (2013.01); *G01R 33/381* (2013.01)

(58) Field of Classification Search
CPC .................................................. G01R 33/3875
USPC .................................................. 324/318, 322
See application file for complete search history.

(56) References Cited

U.S. PATENT DOCUMENTS

| 4,906,934 | A | 3/1990 | Haragashira |
| 5,237,279 | A | 8/1993 | Shimasaki et al. |
| 6,294,972 | B1 | 9/2001 | Jesmanowicz et al. |
| 7,656,155 | B2* | 2/2010 | Tatebayashi ....... G01R 33/4833 324/307 |

(Continued)

FOREIGN PATENT DOCUMENTS

WO    WO2008075051 A1    6/2008

OTHER PUBLICATIONS

Authorized Officer Blaine Copenheaver, International Search Report/Written Opinion in PCT/IB2015/055366 dated Oct. 30, 2015, 10 pages.

*Primary Examiner* — Louis Arana
(74) *Attorney, Agent, or Firm* — Fish & Richardson P.C.

(57) ABSTRACT

Gradient coils are operated to acquire magnetic resonance (MR) signals encoding a first MRI image over a first region inside a main magnet of the MRI system in which at least a portion of a subject is placed, the first region being located within a volume of uniform magnetic field with inhomogeneity below a defined threshold. An active coil is energized to shift the volume of uniform magnetic field such that a second region inside the main magnet of the MRI system is located within the shifted volume of uniform magnetic field, at least a portion of the second region being located outside of the volume of uniform magnetic field before the volume of uniform magnetic field has been shifted. The gradient coil is operated to acquire MR signals encoding a second MRI image over the second region.

20 Claims, 4 Drawing Sheets

(56) References Cited

U.S. PATENT DOCUMENTS

| | | |
|---|---|---|
| 8,552,726 B2 | 10/2013 | Sakakura |
| 9,797,967 B2 * | 10/2017 | Bindseil ............ G01R 33/3875 |
| 2002/0105328 A1 | 8/2002 | Goto et al. |
| 2004/0106865 A1 | 6/2004 | Schuster et al. |
| 2008/0272780 A1 | 11/2008 | Thompson et al. |
| 2009/0124884 A1 | 5/2009 | Saunders et al. |
| 2011/0260727 A1 | 10/2011 | Punchard et al. |
| 2012/0268119 A1 | 10/2012 | Abe et al. |

* cited by examiner

ACTIVE COIL TO SHIFT A VOLUME OF UNIFORM MAGNETIC FIELD

CROSS-REFERENCE TO RELATED APPLICATIONS

This application is a continuation of U.S. patent application Ser. No. 14/899,799, filed Dec. 18, 2015, which is a U.S. National Phase Application of International Patent Application No. PCT/IB2015/055366 filed Jul. 15, 2015, the contents of both are hereby incorporated by reference:

BACKGROUND

The present disclosure relates to magnetic resonance imaging.

SUMMARY

In one aspect, some implementations provide a method for operating a magnetic resonance imaging (MRI) system, the method including operating gradient coils to acquire magnetic resonance (MR) signals encoding a first MRI image over a first region inside a main magnet of the MRI system in which at least a portion of a subject is placed, the first region being located within a volume of magnetic field where a field inhomogeneity is below a defined threshold; energizing an active coil to shift the volume of magnetic field such that a second region inside the main magnet of the MRI system is located within the shifted volume of magnetic field, at least a portion of the second region being located outside of the volume of magnetic field before the volume of magnetic field has been shifted and at least a portion of the first region being located outside of the shifted volume of magnetic field after the volume of magnetic field has been shifted; and operating the gradient coils to acquire MR signals encoding a second MRI image over the second region.

Implementations may include the following features. For example, energizing the active coil may include energizing the active coil while operating the gradient coils to acquire the second MRI image. In another example, energizing the active coil may include energizing the active coil prior to operating the gradient coils to acquire the second MRI image. In yet another example, energizing the active coil includes driving the active coil with at least 2 amperes of electrical current. In still another example, energizing the active coil may include cooling the active coil by running liquid coolant to the active coil.

Some implementations may additionally include operating a shim coil to compensate susceptibility differences inside the portion of the subject located within the shifted volume of magnetic field with inhomogeneity below the defined threshold. In these implementations, operating the shim coil may further include operating the shim coil while operating the gradient coils to acquire MR signals encoding the second MRI image.

In another aspect, some implementations provide a magnetic resonance imaging (MRI) system, including a housing having a bore in which at least a portion of a subject to be imaged is placed; a main magnet accommodated by the housing and configured to generate a volume of magnetic field with inhomogeneity below a defined threshold to form an MRI image over a region located within the volume of magnetic field; an active coil that when energized causes the volume of magnetic field to shift in location and transform in shape; pulse generating coils to generate and apply radio frequency (RF) pulses in sequence to scan the portion of the subject; gradient coils to provide perturbations to the volume of magnetic field such that MRI signals encoding an MRI image are acquired in response to the applied RF pulses; and a control unit coupled to the MRI system and configured to: operate the gradient coils to acquire MR signals encoding a first MRI image over a first region inside the main magnet in which the portion of the subject is placed, the first region being located within the volume of magnetic field in which a field inhomogeneity is below the defined threshold to form the first MRI image; energize the active coil to shift the volume of magnetic field with inhomogeneity below the defined threshold such that a second region inside the main magnet of the MRI system is located within the shifted volume of magnetic field in which the field inhomogeneity is below the defined threshold, at least a portion of the second region being located outside of the volume of magnetic field before the volume of magnetic field has been shifted and at least a portion of the first region being located outside of the shifted volume of magnetic field after the volume of magnetic field has been shifted; and operate the gradient coils to acquire MR signals encoding a second MRI image over the second region being located within the shifted volume of magnetic field in which the field inhomogeneity is below the defined threshold to form the second MRI image.

Implementations may include one or more of the following features. The active coil and the gradient coils may be integrated into one mechanical assembly. The integrated coil assembly may include one liquid cooling system for both the active coil and the gradient coils. The active coil may be constructed as a removable module configured to be mounted along with a gradient assembly that houses the gradient coils. The active coil and the gradient coil may be separately cooled by respective liquid cooling systems. The respective cooling system may incorporate a reservoir holding liquid helium or liquid nitrogen.

The active coil may be constructed on an RF coil assembly configured to be mounted inside the gradient coils. The active coil and the gradient coils may be separately cooled by respective liquid cooling systems. The cooling system may incorporate a reservoir holding liquid helium or liquid nitrogen.

Some implementations may include a group of shimming coils placed around the housing and configured to compensate susceptibility differences inside the portion of the subject located within the volume of magnetic field. The control unit may be further configured to energize the active coil to shift the volume of magnetic field wherein variations in magnetic field strength within the volume of magnetic field are below the defined threshold. The control unit may be further configured to energize the active coil to shift the volume of magnetic field wherein a free induction decay (FID) signal from the volume of magnetic field has a spectral width that is below the defined threshold.

The details of one or more aspects of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference symbols in the various drawings indicate like elements.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

According to selected embodiments of the present disclosure, a magnetic resonance imaging system can include an active coil, for example, integrated with gradient coils as one mechanical assembly, to function as a location-specific static field shim coil which, when activated, moves the volume of uniform magnetic field within the solenoid magnet such that the imaging region where main field inhomogeneity is below a defined threshold is shifted. The active coil is different from the main field shimming coils that are configured to compensate for susceptibility differences caused by air-tissue interfaces, implanted devices, etc. Main field shimming coils generally cannot shift aside a volume of uniform magnetic field suitable for forming an MRI image with sufficient quality. The active coil as disclosed in some implementations may incorporate higher amperage current than those used for the shifting operation. In some instances, the active coil may include active cooling using coolants such as liquid nitrogen or liquid helium. The active coil operates differently than the gradient coil in that, once the active coil is activated, the shifted region of uniform magnetic field stays static whereas turning on the gradient coil initiates a dynamic fluctuation to the main magnetic field such that MRI signals encoding magnetization signals from various portions of the subject can be acquired, based on which an image reconstruction can be performed to yield an MRI image.

Some implementations may allow an operator, such as a clinician, to shift the image region from an initial region that covers, for example, the head area, to a different region that includes, for example, the neck area. More specifically, the patient may be placed in the main magnet and a first image is obtained from the head area. After determining that the neck area warrants further investigation, the operator may activate the active coil to shift the region of uniform magnetic field from the initial region to the different region that includes the neck area. When the shift is in place, the operator may obtain an MRI image of the neck area. This shifting approach may be advantageous for smaller magnets, in which it is less practical to move the patient's neck inward due to limitations in magnet size and shape.

Figure 1A:
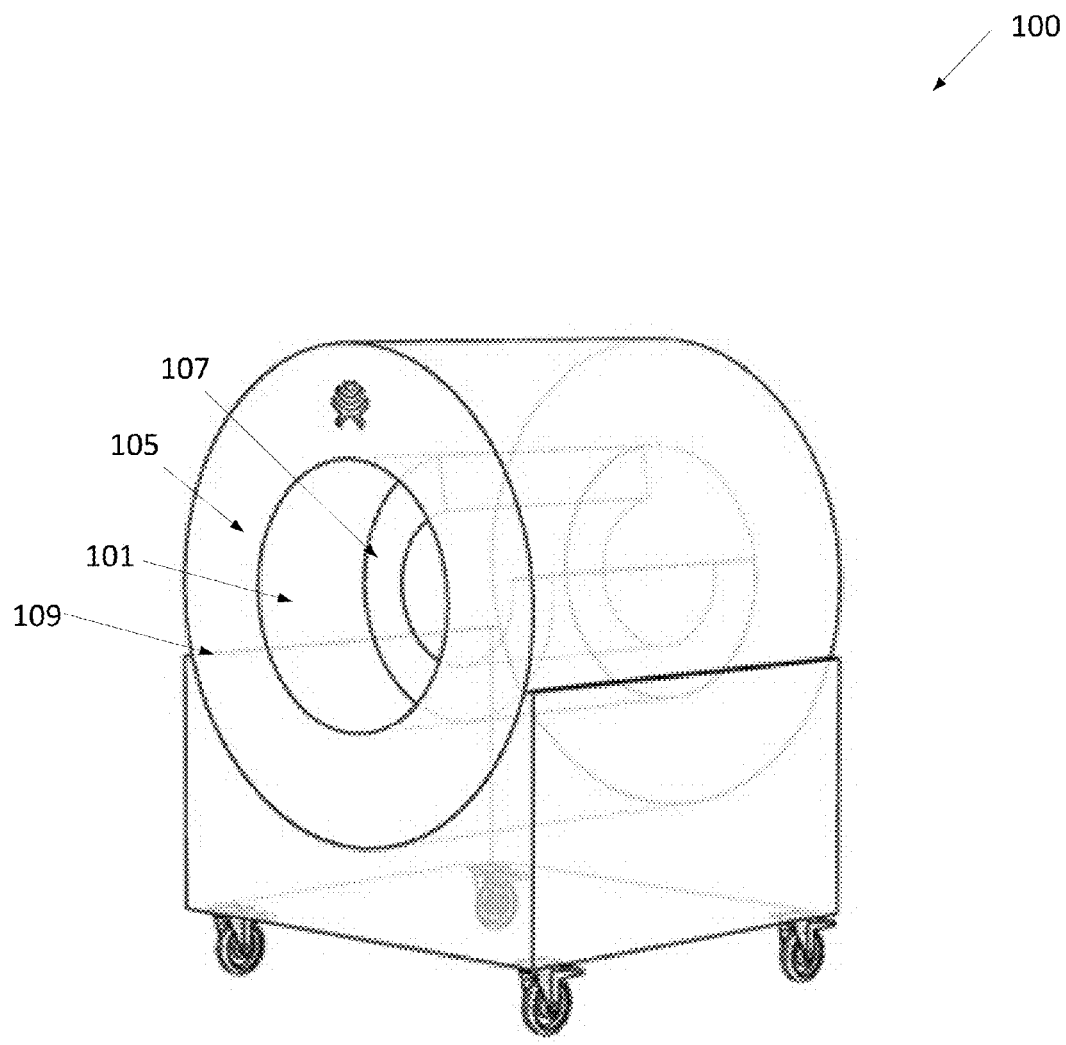
FIG. 1A shows a perspective view of an example of a magnetic resonance imaging (MRI) system with a solenoid magnet where an active coil is provided to shift a volume of uniform magnetic field inside the solenoid magnet.
Figure 1B:
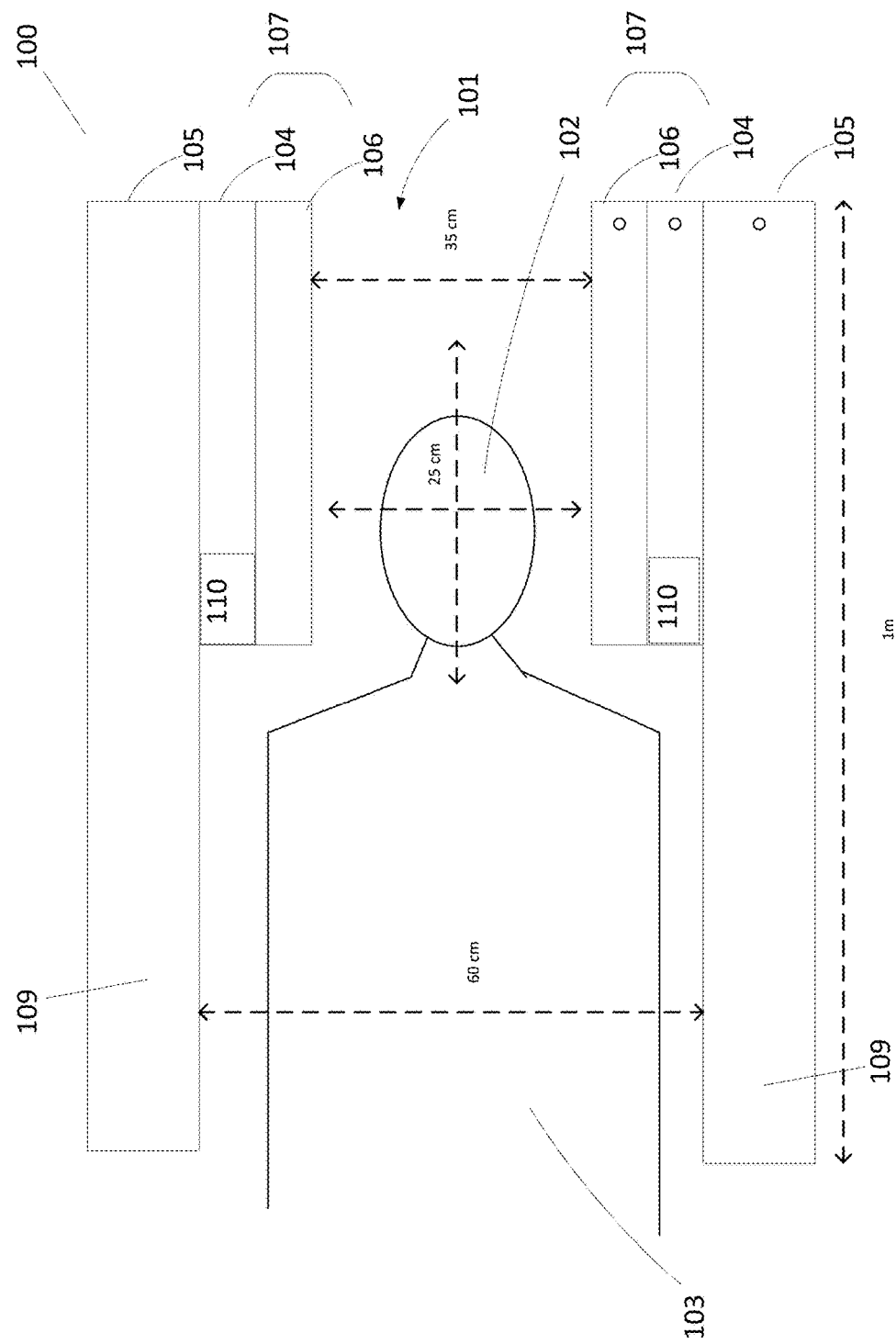
FIG. 1B shows a cross-sectional illustration of the example of a magnetic resonance imaging (MRI) system where the active coil is provided to shift the volume of uniform magnetic field.

FIGS. 1A-1B show a perspective view and a cross-sectional view of an example of a magnetic resonance imaging (MRI) system 100 in which a solenoid magnet 105 is provided in a cylindrical shape with an inner bore 101. Coil assembly 107, including transmit coil 106 and gradient coil 104, is provided within solenoid magnet 105. Coil assembly 107 may generally be shaped as an annular structure and housed within the inner bore of solenoid magnet 105. In some implementations, annular coil assembly 107 only includes gradient coil 104. Gradient coil 104 generally provides field gradients in more than one directions, such as, for example, all three orthogonal spatial directions. Thus, gradient coil 104 may refer to three sets of coils, each configured to generate field fluctuations in a respective direction for the main field in the inner bore of the solenoid magnet 105. Such field fluctuations may cause magnetizations from various spatial locations to experience precessions at different frequencies, enabling encoding of spatial information of the magnetizations through RF excitation pulses.

In these implementations, annular coil assembly does not include transmit coil 106 or any receiver coil. For these implementations, radio-frequency (RF) excitation pulses are, for example, transmitted by local coils for imaging the head region 102 of patient 103. In one instance, a head coil in a birdcage configuration is used for both transmitting RF excitation pulses and receiving MR signals for imaging the subject. In another instance, a surface coil is used for transmitting an RF excitation pulse into the subject and a phased array coil configuration is used for receiving MR signals in response.

In some implementations, shimming coils 109 are housed within the cylindrical walls of solenoid magnet 105. Shimming coils 109 are powered by a group of power amplifiers. In some cases, the power amplifiers are housed in a control room and are connected to shimming coils 109 to provide shimming of the magnetic field within inner bore 101. In driving shimming coils 109, power amplifiers may be controlled by a control unit that generally includes one or more processors as well as programming logic to configure the power amplifiers. In some instances, the control unit is housed in a control room separate from the solenoid magnet 105 of the MRI system 100. The driving current for shimming coils 109 may be in the range of hundreds of miliamperes and generally may not exceed 1 ampere. Further, shimming coils 109 may not require active cooling using circulating coolant. In these implementations, an array of shimming coils can be used to provide adjustment to the field strength within the inner bore 101 such that the magnet field within the inner bore 101 becomes more homogenous.

The embodiments provided herein may be adapted for intraoperative MRI, and MRI systems for use in an emergency room setting. Such MRI systems may include a smaller and more compact bore size magnet compared to the magnets from conventional whole body scanners. One consequence of a smaller bore magnet is that, the volume of uniform magnetic field suitable for imaging (e.g., with field inhomogeneity below a defined threshold) may not cover all areas of interest. As discussed in further detail below, the defined threshold may refer to a variation of magnetic field over a spatial length, or a spectral width of a free-induction signal (FID) emitting from the particular volume. For example, while the head region of a subject may be inside the volume of uniform magnetic field, the neck region of the subject may be not. Yet, the bore size limitation may not allow the subject to be moved further inside the inner bore of the magnet. Some implementations provide an active coil 110 that, once activated, causes the volume of uniform magnetic field to shift in order to accommodate, for example, imaging the neck region of the subject when, for example, it is impractical to move the subject further inside the bore of the magnet. In other words, active coil 110 can provide a location specific static shift of the uniform magnetic field suitable for imaging.

For context, the main magnet of MRI system 100 generates a highly uniform static magnetic field over a certain volume for imaging purposes. Small static field variations on the order of parts-per-million (ppm) can be tolerated; however, it is not possible to generate MR data in locations where the main field deviates too greatly, for example, over hundreds of parts per million (ppms) over a 20-cm diameter spherical volume. The region of uniformity, also referred to as the uniform magnetic field or main field homogeneity, is typically characterized by the maximum static field deviation over a certain spherical volume. For example, 40 ppm over a 25-cm diameter spherical volume (DSV) would represent a maximum $\Delta B0=B0_{max}-B0_{min}=20\,\mu T$ field deviation at a static field of $B0=0.5$ T. The main magnet is designed to achieve a specific homogeneity (that is, the main magnet is designed to have an inhomogeneity below the threshold); however, the actual homogeneity at the installation site may be affected by material in or around the MRI scanner. At the time of installation, passive and/or active shims may be applied to improve the homogeneity so that it meets the specific homogeneity the main magnet is designed to achieve before subjects are placed in the inner bore 101. When a subject (i.e. a human head) is inserted into the MRI scanner, the tissue and any implantable devices in the subject may also affect the homogeneity of the imaging volume and the homogeneity is again typically improved through fine adjustment of active shim coils, such as for example, through shimming coils 109, so that the specific homogeneity is met. To quantify main field homogeneity, some implementations may measure, for example, the spectral width of the free induction decay (FID) signal from the region of interest. In this measure, field homogeneity may hinge on the spectral width of the FID signal to be below a defined threshold. More specifically, if the spectral width of the FID signal is satisfactorily narrow for the desired imaging application, for example, below a defined spectral width value, shimming may be deemed satisfactory. Otherwise, additional shimming may be performed to further reduce the spectral width of the FID signal.

In this context, for a whole body MRI scanner, the bore is wide enough any part of a human can be moved to within the volume of uniform magnetic field. In such systems, the subject can be moved so that the anatomy interest is located in the center of the region of uniformity. For a smaller-bore MRI scanner designed to image the head, geometric constraints limit what parts of the body can be moved into the volume of uniform magnetic field. For example, the geometry of a head-only MRI system could be such that an average human could be positioned so that the region of uniformity generally extends only to the bottom of the chin and for regions further out, the inhomogeneity of the main field may exceed a defined threshold and does not permit MR imaging with the desired quality. The decay in image quality may manifest as poor signal-to-noise ratio, low peak value of the free induction decay (FID) signal, etc. Generally, imaging anatomy farther down the neck or spine for such a person may not be feasible because such regions cannot be placed physically further into the inner bore 101 of scanner.

As noted above, active coil 110, when energized, can provide a location specific static shift of the homogenous region. In this example, active coil 110 could be energized during collection of MR signals from locations in the neck and spine where the main field might otherwise be too inhomogeneous for acquiring MR signals of decent quality. Active coil 110 may, in general, change the shape and location of the region of uniformity such that the volume of uniform magnetic field is shifted from the head area to enclose parts of the neck and spine.

Figure 2:
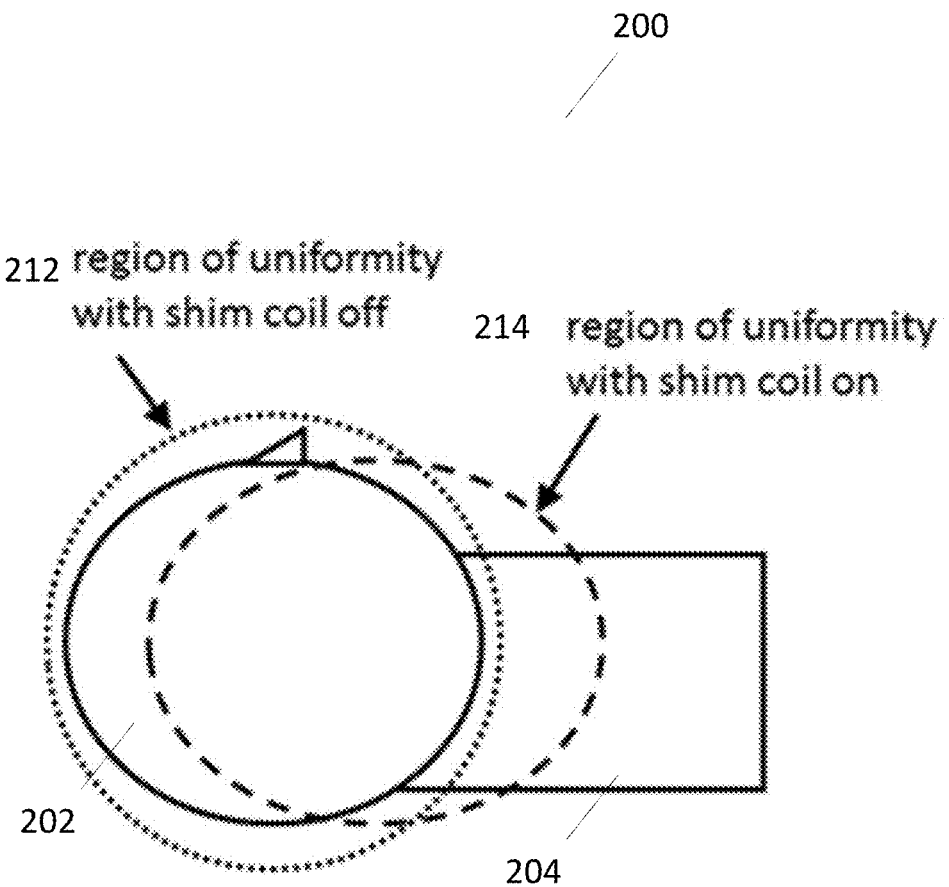
FIG. 2 illustrates an example of shifting the volume of uniform magnetic field inside the solenoid magnet of the MRI system.

FIG. 2 illustrates an example of shifting the volume of uniform magnetic field inside the solenoid magnet of the MRI system 100. Initially, a subject's head area 202 and neck area 204 are inserted into inner bore 101 of MRI system 100 for an imaging session. A first MRI image may be formed for the head area 202 with a portion of neck area 204. As illustrated, the volume of uniform magnetic field (i.e., regions of uniformity 212 when coil off) does not extend from the head area 202 to fully cover the neck area 204. Yet, the shape and the size of inner bore 101 prevents the subject to be further inserted, as noted earlier. In this illustration, the clinician can, through a control panel on MRI system 100, energize active coil 110 to shift the volume of uniform magnetic field toward the neck area 204 so that the shifted volume of uniform magnetic field (i.e., region of uniformity with coil on 214) fully covers neck area 204. Once the uniform magnetic field covers neck area 204 such that main field inhomogeneity within neck area 204 falls under a defined threshold value, the clinician can initiate, through the control panel on MRI system 100, a normal scan using gradient coil 104, RF coil 106, and shim coil 109 to obtain a desired image of neck area 204.

In some instances, active coil 110 could remain energized for the entire data collection if the shifted volume of homogeneity encloses all parts of the requested imaging volume. In other instances, active coil 110 may be turned on and off in an interleaved manner if the requested imaging volume spans both locations where the active coil 110 needs to be off and locations where active coil 110 needs to be on. In the illustration of FIG. 2, when active coil 110 is energized, the main field homogeneity near the top of the head may be sacrificed to enable the region of uniformity to extend deeper into neck area 204. In some configurations, the extent of the shift is adjustable to accommodate the exact reach into neck area 204. For example, the clinician, through the control panel on MRI system 100, may change the energization level of active coil 110 to a particular level that corresponds to a degree of shift into neck area 204. The correspondence may be estimated beforehand and stored in a look-up table for access during an imaging session.

In the illustration of FIG. 1B, active coil 110 is housed within the enclosure for gradient coil 104. In this configuration, active coil 110 may share the same active cooling with gradient coil 104. For example, both active coil 110 and gradient coil 104 may be cooled using the same cooling system circulates coolant such as a liquid helium of liquid nitrogen. This configuration may leverage an existing cooling system that already includes a reservoir for liquid coolant such as liquid nitrogen or liquid helium. The driving current for active coil 110 may be in the range of 1-10 amperes while the gradient coil 104 may require driving current higher than 10 amperes. In other instances, active coil 110 may be constructed on RF coil 106 and configured to be mounted inside gradient coil 104. In other instances, active coil 110 can be housed in the side wall 105 of the magnet and may require a separate cooling system. In the illustrations above, active coil 110 may couple to a control unit on MRI system 100, for example, through power amplifiers that provide the driving currents. The control unit may be housed in a separate control room away from the magnet. The control unit may include processors or programming logic to configure the power amplifiers that drive active coil 110.

Figure 3:
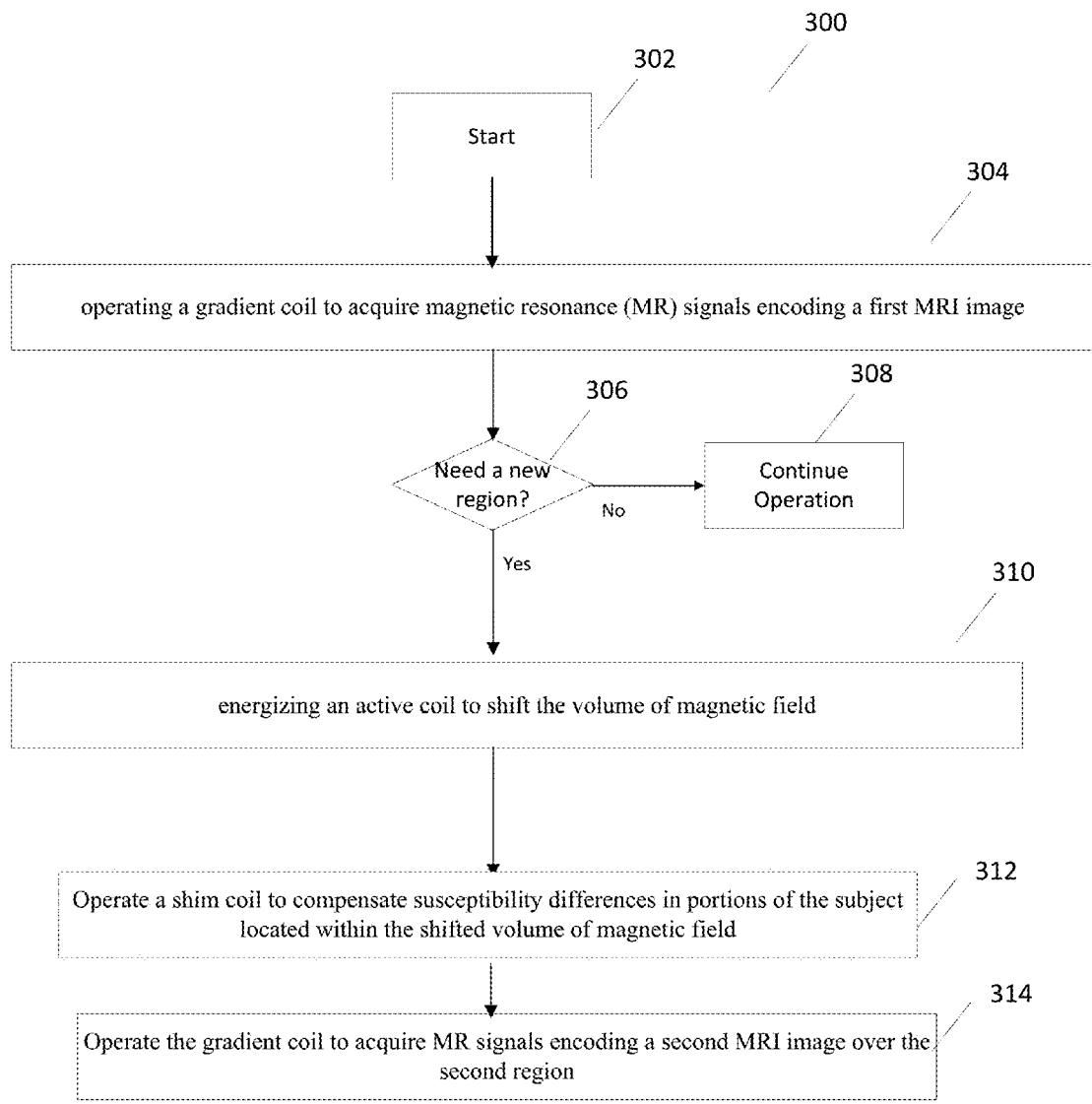
FIG. 3 shows an example of operating the MRI system with the active coil to shift the volume of uniform magnetic field when imaging a subject.

FIG. 3 shows an example of a flow chart 300 for operating the active coil 110 of MRI system 100. When the process flow initiates (302), a gradient coil 104 may be operated to acquire magnetic resonance (MR) signals encoding a first MRI image over a first region inside a main magnet of the MRI system in which at least a portion of a subject is placed, the first region being located within a volume of uniform magnetic field with inhomogeneity below a defined threshold (304). The defined threshold may refer to a ceiling level of the delta of the main magnetic field over a span of distance, for example, 20 µT/25 cm for a 0.5 T main magnet. The defined threshold may also refer to an upper bound of the spectral width of the FID signal from a desired volume. For example, the spectral width may be measured as the full width half maximum (FWHM) width. The operation may be initiated by an operator configuring scanning parameters on a control panel. The gradient coil may be coupled to a control unit of the MRI system 100 to receive instructions such that gradient waveforms are played accordingly to provide field fluctuations to the main magnetic field. As noted earlier, gradient coil 104 may incorporate more than one subset of gradient coils, each operating to effectuate field fluctuations in one spatial direction inside inner bore 101 of MRI system 100. The first image may reveal the subject's head area 202, with portions from neck area 204. When acquiring the MR signals encoding the first MRI image, shimming coil 109 may be used to compensate for susceptibility differences within, for example, head area 202 and the portions from neck area 204.

Next, a determination may be made as to whether a new scan is required (306), for example, to reveal further details of neck area 204 in addition to what has been portrayed on the first image, or to look further into neck area 204. In some instances, the determination may be made based on an input from an operator of MRI system 100. Other instances may incorporate an automatic region shifting aspect. For example, MRI system 100 may perform image recognition of the first MRI image and determine where certain anatomical features in neck area 204 are not fully captured and shifting the volume of uniform magnetic field is thus warranted. It may be determined the volume of uniform magnetic field covers the portions of interest from neck area 204 and there is no need to look further, in which case, MRI system 100 may continue operation without engaging active coil 110 (308).

When shifting is warranted, a control unit on MRI system 100 may energize an active coil to shift the volume of uniform magnetic field such that a second region inside the main magnet of the MRI system is located within the shifted volume of uniform magnetic field, at least a portion of the second region being located outside of the volume of uniform magnetic field before the volume of uniform magnetic field has been shifted and at least a portion of the first region being located outside of the shifted volume of uniform magnetic field after the volume of uniform magnetic field has been shifted (310). The shifting may leave the shifted volume of uniform magnetic field covering, for example, the portions of interest from neck area 204. As noted above, a particular energization level can lead to a particular shift. Energizing active coil 110 may involve running currents in the range of 1-10 amperes while shimming coil 109 is associated with driving currents in the sub-ampere range, such as hundreds of milliamperes. Meanwhile, gradient coil 104 may generally be driven by electrical currents in the 10-100 ampere range and may generally require active cooling via circulating coolants.

Once the volume of uniform magnetic field has been shifted to, for example, cover portions of interest from neck area 204, a shim coil can be operated to compensate susceptibility differences in the portion of the subject located within the shifted volume of uniform magnetic field (312). Once shimming is in place, gradient coil 104 may be operated to provide field fluctuations to the main magnetic field such that MR signals can be acquired that encode a second MRI image over the second region located within the shifted volume of uniform magnetic field (314).

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method for operating a magnetic resonance imaging (MRI) system, the method comprising:
    operating gradient coils while turning off an active coil to acquire first magnetic resonance (MR) signals encoding a first MRI image with a first field of view, the first MR signals emitted from a first region inside a main magnet of the MRI system in which at least a portion of a subject is placed; and
    energizing the active coil to shift the volume of magnetic field such that second MR signals are acquired from a second region inside the main magnet of the MRI system,
    wherein the first region is located within a volume of magnetic field while the second region is located within the shifted volume of magnetic field, and wherein the first region and the second region are both sufficiently homogeneous in field strength such that a field inhomogeneity of each region is within below a defined threshold.

2. The method of claim 1, further comprising:
    combining the first MRI image with a second MRI image reconstructed from the second MR signals such that the first field of view is extended to include at least a portion of the second region located outside the volume of magnetic field before the volume of magnetic field has been shifted.

3. The method of claim 1, further comprising:
reconstructing a second MRI image from the second MR signals acquired from the second region such that the second MRI image is generated with a reduced field of view compared to the first MRI image.

4. The method of claim 1, further comprising:
operating the gradient coils while turning off the active coil to acquire third magnetic resonance (MR) signals encoding a third MRI image with a third field of view; and
energizing the active coil to shift the volume of magnetic field such that fourth MR signals are acquired from a fourth region inside the main magnet of the MRI system.

5. The method of claim 4, wherein the third field of view and the first field of view substantially overlap each other while the fourth field of view and the second field of view substantially overlap each other.

6. The method of claim 1, wherein operating the gradient coils comprises:
operating the gradient coils to generate gradient waveforms in tandem with at least one radio-frequency (RF) pulse such that the first MR signals include a spin-echo signal and the second MR signals also include a spin-echo signal.

7. The method of claim 1, wherein energizing the active coil comprises:
energizing the active coil while operating the gradient coils to acquire the second MR signals.

8. The method of claim 1, wherein energizing the active coil comprises:
energizing the active coil prior to operating the gradient coils to acquire the second MR signals.

9. The method of claim 1, further comprising: operating a shim coil while operating the gradient coils to compensate susceptibility differences inside the portion of the subject located within the shifted volume of magnetic field with inhomogeneity below the defined threshold.

10. A magnetic resonance imaging (MRI) system, comprising:
a housing having a bore in which at least a portion of a subject to be imaged is placed;
a main magnet accommodated by the housing and configured to generate a volume of magnetic field;
an active coil that when energized causes the volume of magnetic field to shift in location and transform in shape;
pulse generating coils configured to generate and apply radio frequency (RF) pulses in sequence to scan the portion of the subject;
gradient coils configured to provide perturbations to the volume of magnetic field such that magnetic resonance (MR) signals encoding an MRI image are acquired in response to the applied RF pulses; and
a control unit coupled to the MRI system and configured to:
operate gradient coils while turning off an active coil to acquire first magnetic resonance (MR) signals encoding a first MRI image with a first field of view, the first MR signals emitted from a first region inside a main magnet of the MRI system in which at least a portion of a subject is placed; and
energize the active coil to shift the volume of magnetic field such that second MR signals are acquired from a second region inside the main magnet of the MRI system,
wherein the first region is located within the volume of magnetic field while the second region is located within the shifted volume of magnetic field, and wherein the first region and the second region are both sufficiently homogeneous in field strength such that a field inhomogeneity of each region is within below a defined threshold.

11. The MRI system of claim 10, wherein the active coil and the gradient coils are integrated into one mechanical assembly.

12. The MRI system of claim 10, wherein the active coil is constructed as a removable module configured to be mounted along with a gradient assembly that houses the gradient coils.

13. The MRI system of claim 10, wherein the active coil is constructed on an RF coil assembly configured to be mounted inside the gradient coils.

14. The MRI system of claim 10, further comprising: a group of shimming coils placed around the housing and configured to compensate susceptibility differences inside the portion of the subject located within the volume of magnetic field.

15. The MRI system of claim 10, wherein the control unit is further configured to:
combine the first MRI image with a second MRI image reconstructed from the second MR signals such that the first field of view is extended to include at least a portion of the second region located outside the volume of magnetic field before the volume of magnetic field has been shifted.

16. The MRI system of claim 10, wherein the control unit is further configured to:
reconstruct a second MRI image from the second MR signals acquired from the second region such that the second MRI image is generated with a reduced field of view compared to the first MRI image.

17. The MRI system of claim 10, wherein the control unit is further configured to:
operate the gradient coils while turning off the active coil to acquire third magnetic resonance (MR) signals encoding a third MRI image with a third field of view; and
energize the active coil to shift the volume of magnetic field such that fourth MR signals are acquired from a fourth region inside the main magnet of the MRI system.

18. The MRI system of claim 17, wherein the third field of view and the first field of view substantially overlap each other while the fourth field of view and the second field of view substantially overlap each other.

19. The MRI system of claim 17, wherein the control unit is further configured to:
energize the active coil while operating the gradient coils to acquire the second MR signals.

20. The MRI system of claim 17, wherein the control unit is further configured to:
energize the active coil prior to operating the gradient coils to acquire the second MR signals.

* * * * *